(12) United States Patent
Tamames, III

(10) Patent No.: US 10,729,127 B2
(45) Date of Patent: *Aug. 4, 2020

(54) RODENTICIDE BINDING SYSTEM

(71) Applicant: SPECIAL NUTRIENTS, LLC, Miami, FL (US)

(72) Inventor: Fernando Tamames, III, Key Biscayne, FL (US)

(73) Assignee: Special Nutrients, LLC, Miami, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/727,877

(22) Filed: Oct. 9, 2017

(65) Prior Publication Data

US 2018/0092354 A1    Apr. 5, 2018

Related U.S. Application Data

(63) Continuation-in-part of application No. 15/070,243, filed on Mar. 15, 2016, now Pat. No. 10,058,568.

(60) Provisional application No. 62/164,819, filed on May 21, 2015.

(51) Int. Cl.

| | | |
|---|---|---|
| *A01N 25/08* | (2006.01) | |
| *A01N 43/12* | (2006.01) | |
| *C01B 33/40* | (2006.01) | |
| *A61K 35/10* | (2015.01) | |
| *A61K 33/06* | (2006.01) | |
| *A61K 33/12* | (2006.01) | |
| *A23K 20/28* | (2016.01) | |
| *A01N 25/00* | (2006.01) | |
| *A23K 50/50* | (2016.01) | |
| *C05G 3/60* | (2020.01) | |

(52) U.S. Cl.
CPC .......... *A01N 25/08* (2013.01); *A01N 25/004* (2013.01); *A01N 43/12* (2013.01); *A23K 20/28* (2016.05); *A23K 50/50* (2016.05); *A61K 33/06* (2013.01); *A61K 33/12* (2013.01); *A61K 35/10* (2013.01); *C01B 33/40* (2013.01); *C05G 3/60* (2020.02); *A01N 2300/00* (2013.01)

(58) Field of Classification Search
CPC ........ A61K 33/06; A61K 33/12; A61K 35/10; A61K 2300/00; A23K 20/28; A01N 25/004; A01N 43/12; A01N 25/08; A01N 43/16; A01N 2300/00; C01B 33/40; C05G 3/02
See application file for complete search history.

(56) References Cited

U.S. PATENT DOCUMENTS

| | | | |
|---|---|---|---|
| 3,586,478 A | 6/1971 | Neumann | |
| 5,639,492 A * | 6/1997 | Turk | A23K 20/28 426/2 |
| 5,935,623 A * | 8/1999 | Alonso-Debolt | A23K 50/30 424/438 |
| 6,827,959 B1 | 12/2004 | Schall et al. | |
| 7,066,998 B2 | 6/2006 | Rohrbaugh et al. | |
| 8,507,019 B2 | 8/2013 | Schoeters et al. | |
| 10,058,568 B2 * | 8/2018 | Tamames, III | A61K 35/10 |
| 2009/0170705 A1 | 7/2009 | Nennemann | |
| 2011/0135796 A1 * | 6/2011 | Chang | A23L 3/358 426/323 |
| 2011/0281018 A1 * | 11/2011 | Schoeters | A23K 20/111 426/654 |
| 2012/0291793 A1 * | 11/2012 | Byrd | A24B 15/241 131/332 |
| 2013/0203595 A1 * | 8/2013 | Fowler | B01J 13/0034 504/117 |
| 2013/0231380 A1 * | 9/2013 | Bowman | A01N 25/004 514/407 |
| 2016/0339056 A1 | 11/2016 | Tamames, III | |

FOREIGN PATENT DOCUMENTS

WO     1991013555     9/1991

OTHER PUBLICATIONS

Garcia-Sirera, Josep, "Endotoxins in swine-effects and strategies for control" International Pig Topics, vol. 25, No. 3, 2010, 4 pages.
Non-Final Office Action for U.S. Appl. No. 15/070,243 dated May 5, 2017.
Schaumberger et al. "Evaluation of the endotoxin binding efficiency of clay minerals using the Limulus Amebocyte lysate test: an in vitro study" in AMB Express, 2014, 4:1.
Final Office Action for U.S. Appl. No. 15/070,243 dated Oct. 27, 2017.

* cited by examiner

*Primary Examiner* — Blessing M Fubara
(74) *Attorney, Agent, or Firm* — Kowert, Hood, Munyon, Rankin & Goetzel, P.C.; Mark R. DeLuca

(57) ABSTRACT

In some embodiments, a composition and/or method may include a rodenticide binding system formulated for safe and effective mixture into various feed rations which are fed to monogastric and ruminant animals such as poultry, swine, cows, cattle, and fish, among others. The rodenticide binding system includes novel combinations of one or more of an organoclay, an activated hydrated sodium calcium aluminosilicate clay, and a synthetic hectorite clay. In some embodiments, the binding composition may include organoclay, bentonite, hectorite, Leonardite, and/or any combination thereof. The toxin binding complex may effectively bind some pesticides (e.g., rodenticides) in the animal's digestive system, preventing their absorption and the consequent damages to the animal.

8 Claims, No Drawings

RODENTICIDE BINDING SYSTEM

PRIORITY CLAIM

This application is a continuation-in-part of U.S. patent application Ser. No. 15/070,243 entitled "TOXIN BINDING SYSTEM" filed on Mar. 15, 2016, which claims priority to U.S. Provisional Patent Application No. 62/164,819 entitled "MYCOTOXIN BINDING SYSTEM" filed on May 21, 2015, all of which is incorporated by reference herein.

BACKGROUND OF THE INVENTION

1. Field of the Invention

The present disclosure generally relates to a toxin binding system. More particularly, the disclosure generally relates to a rodenticide binding system which may be safely and effectively mixed into animal feed to bind with rodenticides.

2. Description of the Relevant Art

Fungal contamination of animal feed is often unavoidable and is a serious concern given that many of these contaminants include toxic metabolites known as mycotoxins. Mycotoxin contamination can occur in a crop growing in the field, or contamination may be introduced during harvest, storage and/or processing of the animal feed for use in raising monogastric and ruminal animals. Mycotoxins are fairly stable compounds often found in animal feed for monogastric and ruminal animals, and they are a known cause of a wide variety of deleterious effects in these animals. Agricultural pesticides are other common contaminants of animal feed. Endotoxins are not natural contaminants of feedstuffs. Feedstuffs can be contaminated with endotoxins when mixed with products of animal origin. Endotoxins are another type of toxin, of bacterial origin, which are commonly found in the gastrointestinal tract of livestock, and pesticides are commonly found in the foodstuffs fed to various types of livestock, and as a result, have been known to have toxic effects on livestock.

Mycotoxins are known to cause toxic, teratogenic, mutagenic, and carcinogenic effects, and have been linked to a depression of the animal's immune system. Furthermore, mycotoxins can affect different organs in an animal: urinary, digestive, nervous, reproductive, and immune systems, and as such, it makes it more difficult to establish a precise diagnosis once an animal is affected. The effects of mycotoxins, depends on the level of contamination, the presence of one or more toxins, the type of animal, its age, the time of exposure, genetic makeup, and its nutritional and health status at the time of exposure to contaminated feed.

The most dangerous mycotoxins affecting animals are aflatoxin, ochratoxin, T-2 toxin, fumonisin, and deoxynivalenol, also known as DON. These mycotoxins, along with other trichothecene mycotoxins, can also affect monogastric and ruminants, to greater or lesser degrees.

Clays have historically been added to feed to solve the problem of mycotoxin contamination. Once bound by the clay in the gastrointestinal track, the mycotoxins are discharged in the animal's excrement with little to no harm to the animal. Another material, hydrated sodium calcium aluminosilicate clay, has also been added to animal feeds, and similarly, has proven successful in binding mycotoxins in the animal's digestive system, such that they may be safely discharged from the animal's body. More in particular, these clays have been found to act as enterosorbents that tightly and selectively bind these poisons in the gastrointestinal tract of animals, decreasing their bioavailability and associated toxicities.

Agricultural pesticide (e.g., herbicides, insecticides, rodenticides) ingestion by certain animals can be a particular problem especially if the animals ingesting the pesticide include domesticated food animals. One example of domesticated food animals which has been particularly effected are swine, due to their ingestion of rodenticides. Accidental ingestion of rodenticides in animals-represents significant food safety concerns, animal welfare issues, as well as substantial economic losses to the animal producers.

The emergence of rodent strains resistant to older or first generation anticoagulant rodenticides has spawned the development of more potent, second generation compounds (e.g., bromadiolone), which increases the potential for toxicity following accidental ingestion and the contamination of-animal carcasses intended for consumption.

Reports of accidental rodenticide ingestion, or possible exposure, in animals usually involve pigs near market weight and typically include groups containing large numbers of pigs.

Therefore a composition and/or method which provide a toxin binding capacity which may be safely mixed into animal feeds and capable of binding with pesticides (e.g., rodenticides) in the animal's digestive tract would be highly desirable. It would be even more advantageous to provide a toxin binding system which may be safely mixed into animal feed and capable of binding with mycotoxins inside the animal's mouth as well as at the animal's gastrointestinal tract level. Yet a further benefit may be obtained by providing a toxin binding system which is also effective in binding other toxins such as pesticides (e.g., rodenticides).

SUMMARY

In some embodiments, a composition and/or method may include a toxin binding system which may be safely and effectively mixed into animal feed and which may include novel combinations of one or more of an organoclay, an aluminosilicate clay, and a synthetic hectorite clay. In at least one embodiment, the toxin binding system is effective in binding other toxins, such as pesticides (e.g., rodenticide), which may find their way into the gastrointestinal tract of livestock. In some embodiments, the binding composition may include organoclay, bentonite, hectorite, humic acid, and/or any combination thereof.

In some embodiments, a rodenticide binding system may include an amount of an organoclay and an amount of synthetic hectorite clay.

In some embodiments, a rodenticide binding system may include an amount of an aluminosilicate clay and an amount of a synthetic hectorite clay.

In some embodiments, a rodenticide binding system may include an amount of an organoclay, and amount of an aluminosilicate clay, and an amount of a synthetic hectorite clay.

In some embodiments, the rodenticide comprises Brodifacoum, Bromadiolon, Coumatetralyl, Difenacoum, Flocoumafen, or Warfarin.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open-ended relationships and therefore mean including, but not limited to. Similarly, the words "have," "having," and "has" also indicated open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. For example, a "third die electrically connected to the module substrate" does not preclude scenarios in which a "fourth die electrically connected to the module substrate" is connected prior to the third die, unless otherwise specified. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task. In some contexts, "configured to" may be a broad recitation of structure generally meaning performing the task or tasks during operation. As such, the component can be configured to perform the task even when a system is not currently in use.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112 paragraph (f), interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DETAILED DESCRIPTION

Definitions

Unless defined otherwise, all technical and scientific terms used herein have the same meaning as commonly understood by one of ordinary skill in the art.

The term "bentonite" as used herein generally refers to an absorbent aluminium phyllosilicate clay consisting mostly of montmorillonite.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

The term "hectorite" as used herein generally refers to a rare soft, greasy, white clay mineral with a chemical formula of $Na_{0.3}(Mg,Li)_3Si_4O_{10}(OH)_2$.

The term "humic acid" as used herein generally refers to a principal component of humic substances, which are the major organic constituents of soil (humus), peat and coal. It is also a major organic constituent of many upland streams, dystrophic lakes, and ocean water. It is produced by biodegradation of dead organic matter. It is not a single acid; rather, it is a complex mixture of many different acids containing carboxyl and phenolate groups so that the mixture behaves functionally as a dibasic acid or, occasionally, as a tribasic acid.

The term "monogastric" as used herein generally refers to an animal having a simple single-chambered stomach.

The term "mycotoxin" as used herein generally refers to a toxic secondary metabolite produced by organisms of the fungi kingdom, commonly known as molds.

The term "organoclay" as used herein generally refers to an organically modified clay (e.g., an organically modified phyllosilicate), derived from a naturally occurring clay mineral. By exchanging the original interlayer cations for organocations an organophilic surface is generated, consisting of covalently linked organic moieties.

The term "rodenticide" as used herein generally refers to pest control chemicals made and sold for the purpose of killing rodents and other related pests.

The term "ruminant" as used herein generally refers to mammals that are able to acquire nutrients from plant-based food by fermenting it in a specialized stomach compartment (rumen) prior to digestion, principally through microbial actions.

As previously indicated, the compositions are directed to a rodenticide binding composition. More in particular, the present rodenticide binding composition may be formulated for mixture into animal feed which are used as a food source for farming/raising of monogastric and ruminal animals including, but in no manner limited to, poultry, swine, dairy and beef cattle, sheep, goats, horses, and fish. As previously stated, rodenticide contamination can occur, for example, when animals consume dead rats (which have died due to the rodenticide) or they are eating the rat droppings which may contain the rodenticides. Pesticides could also be found in feedstuffs.

In some embodiments, a pesticide (e.g., rodenticide) binding system may include an organoclay. Organoclay may include an organically modified phyllosilicate, derived from a naturally occurring clay mineral. By exchanging the original interlayer cations for organocations an organophilic surface may be generated, capable of binding a wider range of toxins than the original clay, including but not limited to, rodenticides, such as derive from pesticides.

In another embodiment of the present invention, a rodenticide binding system may include an aluminosilicate clay. In at least one embodiment, the aluminosilicate clay may include a sodium calcium aluminosilicate clay. In some embodiments, a rodenticide binding system may include a hydrated sodium calcium aluminosilicate clay, and in one embodiment, an activated hydrated sodium calcium aluminosilicate clay. Bentonite may be included as an example of an aluminosilicate clay.

As will be appreciated by those of skill in the art, both organoclay and activated hydrated sodium calcium aluminosilicate clay are lipophilic, and will bind fats, oils, and other lipids. Organoclays and sodium calcium aluminosilicate clays have been utilized as an additive in animal feeds and have been found to be effective in binding with rodenticide in the gastrointestinal tract of animals including but not limited to poultry, swine, cows, cattle, and fish. The rodenticide binding system has been found to be effective in binding pesticides and certain rodenticides which could find their way into the gastrointestinal tract of animals. In some embodiments, neither organoclay nor activated hydrated sodium calcium aluminosilicate clay bind beneficial constituents inherent within or added to animal feeds, such as, amino acids, vitamins, minerals, antibiotics, pigments, coccidiostats, etc.

In at least one embodiment, a rodenticide binding system may include an amount of a hydrophilic clay. In one embodiment, the present system may include an amount of a synthetic hectorite clay, such as is described in detail in U.S. Pat. No. 3,586,478, which is incorporated herein by reference in its entirety. A synthetic hectorite clay may be readily dispersible in water or other aqueous solvents. In some embodiments, the composition may include naturally occurring hectorite.

As such, a rodenticide binding system may include a combination of both a lipophilic clay, namely, organoclay and/or sodium calcium aluminosilicate, and a hydrophilic clay (e.g., a synthetic hectorite clay). Therefore, the rodenticide binding system may be effective in binding certain pesticides such as rodenticides present in the animal's gastrointestinal tract, such as via contaminated animal feed or rodent carcasses. A rodenticide binding system may be effective in binding rodenticide, such as, by way of example only, Brodifacoum, Bromadiolon, Coumatetralyl, Difenacoum, Flocoumafen, and/or Warfarin. In some embodiments, the rodenticide binding system may bind to the rodenticides Brodifacoum, Bromadiolon, Coumatetralyl, Difenacoum, Flocoumafen, and/or Warfarin with a greater than 80%, 90%, or 95% efficiency. In some embodiments, the rodenticide binding system may bind to the rodenticides Brodifacoum, Bromadiolon, Coumatetralyl, Difenacoum, Flocoumafen, and/or Warfarin with a greater than 90% efficiency. In some embodiments, the rodenticide binding system may bind to the rodenticides Brodifacoum, Bromadiolon, Coumatetralyl, Difenacoum, Flocoumafen, and Warfarin with a greater than 90% efficiency. In some embodiments, the rodenticide binding system may bind to the rodenticides Coumatetralyl with a greater than 90%, 95%, or 99% efficiency. Efficiency (%) is generally defined herein as the % adsorption minus the % desorption of the rodenticide to the composition. In some embodiments, the rodenticide binding system may bind to the rodenticides Brodifacoum, Bromadiolon, Coumatetralyl, Difenacoum, Flocoumafen, and/or Warfarin with a greater than 80%, 90%, or 95% adsorption rate. In some embodiments, the rodenticide binding system may bind to the rodenticides Brodifacoum, Bromadiolon, Coumatetralyl, Difenacoum, Flocoumafen, and Warfarin with a greater than 80%, 90%, or 95% adsorption rate.

An effective rodenticide adsorbent may diminish or prevent the adsorption of rodenticide at the intestinal level and reduce ailments associated with the rodenticide and/or transmission of the rodenticide down the food chain. In some embodiments, the rodenticide binding system may be effective in binding other types of pesticides also present in the gastrointestinal track of the animal via contaminated feedstuffs, contaminated animals and/or feces. In some embodiments, binding systems described herein bind the rodenticides. The bound rodenticides may then be passed through the animal (e.g., in the feces), not allowing the poison to remain in the animal and cause damage and/or accumulate in the meat.

In some embodiments, a rodenticide binding system may include one or more humic acids. In some embodiments, humic acids may be hydrophilic. The humic acid may form between about 0.5% and about 5.0% of the binding composition. In some embodiments, humic acid may be provided by Leonardite. The term humic acid is a generic name. Leonardite comes only from the states of Wyoming, North and South Dakota.

In some embodiments, a rodenticide binding system may include one or more types of bentonite. In some embodiments, bentonite may bind one or more rodenticides. The different types of bentonite are each named after the respective dominant element, such as potassium (K), sodium (Na), calcium (Ca), and aluminium (Al). Bentonite usually forms from weathering of volcanic ash, most often in the presence of water. For industrial purposes, two main classes of bentonite exist: sodium and calcium bentonite. The bentonite may form between about 50% and about 75% of the binding composition.

In some embodiments, any number of the components discussed herein may be combined to form a rodenticide binding system. By combining multiple components discussed herein into a single composition, a composition which binds rodenticides better than the individual components may be achieved. In some embodiments, the binding composition may include organoclay, bentonite, hectorite, humic acid (e.g., Leonardite), and/or any combination thereof.

In some embodiments, the bentonite may form between about 50% and about 75% of the binding composition. In some embodiments, the hectorite may form between about 0.5% and about 5.0% of the binding composition. In some embodiments, the organoclay may form between about 20% and about 40% of the binding composition. In some embodiments, the humic acid (e.g., Leonardite) may form between about 0.5% and about 5.0% of the binding composition.

In some embodiments, a toxin binding system as described in Publication No. US-2016-0339056-A1 entitled "Toxin Binding System" to Tamames III and published on Nov. 24, 2016, incorporated by reference herein, may bind to toxins Aflatoxin, Fumonisin, Ochratoxin, and Zearalenone with an Efficiency of at least 90%, 70%, 90%, and 90% respectively. In some embodiments, a toxin binding system as described in Publication No. US-2016-0339056-A1 may bind to toxins Aflatoxin, Fumonisin, Ochratoxin, and Zearalenone with an Efficiency of at least 95%, 70%, 90%, and 95% respectively. In some embodiments, a toxin binding system as described in Publication No. US-2016-0339056-A1 may bind to toxins Aflatoxin, Fumonisin, Ochratoxin, and Zearalenone with an Efficiency of at least 99%, 70%, 93%, and 98% respectively.

EXAMPLES

Having now described the invention, the same will be more readily understood through reference to the following example(s), which are provided by way of illustration, and are not intended to be limiting of the present invention.

Example 1: Rodenticide Absorbent Sample
Description—MYCO-AD A-Z (COBIND
A-Z-TOXFREE-MYCO-AD Z-T) 1 Apr. 2016
16D01FZX The organoclay may be formed from 64% original bentonite (e.g., about 64%) and surfactant used to modify the original clay surface. The results of these tests are performed under ambient temperature and humidity. These results relate only to the samples tested.

|  | Brodifacoum | Bromadiolon | Coumatetralyl | Difenacoum | Flocoumafen | Warfarin |
|---|---|---|---|---|---|---|
| % Adsorption | 99.2 | 100.0 | 99.8 | 98.8 | 91.0 | 98.2 |
|  | 99.0 | 100.0 | 99.8 | 99.5 | 91.9 | 98.1 |
|  | 99.6 | 100.0 | 99.7 | 99.3 | 91.0 | 98.1 |
| % Adsorption Average | 99.3 | 100.0 | 99.8 | 99.2 | 91.3 | 98.1 |
| % Desorption | 0.3 | 0.0 | 1.6 | 0.2 | 0.0 | 0.9 |
|  | 0.4 | 0.0 | 1.7 | 0.1 | 0.0 | 1.1 |
|  | 0.3 | 0.0 | 1.6 | 0.1 | 0.0 | 1.1 |
| % Desorption Average | 0.3 | 0.0 | 1.6 | 0.1 | 0.0 | 1.0 |
| % Efficiency | 99.0 | 100.0 | 98.2 | 99.1 | 91.3 | 97.1 |

Inclusion Rate: 0.5 kg/ton
Rodenticide Concentration: 5000 ppb
Adsorption pH: 4
Desorption pH: 6.5

Example 2: Rodenticide Absorbent Sample
Description—MYCO-AD A-Z (COBIND
A-Z-TOXFREE-MYCO-AD Z-T) 1 Apr. 2016
16D01FZX The organoclay may be formed from 64% original bentonite (e.g., about 64%) and surfactant used to modify the original clay surface. The results of these tests are performed under ambient temperature and humidity. These results relate only to the samples tested.

|  | Brodifacoum | Bromadiolon | Coumatetralyl | Difenacoum | Flocoumafen | Warfarin |
|---|---|---|---|---|---|---|
| % Adsorption | 99.5 | 100.0 | 100.0 | 99.5 | 98.2 | 99.1 |
|  | 99.6 | 100.0 | 100.0 | 99.5 | 98.8 | 99.3 |
|  | 99.3 | 100.0 | 100.0 | 99.5 | 98.2 | 99.2 |
| % Adsorption Average | 99.5 | 100.0 | 100.0 | 99.5 | 98.4 | 99.2 |
| % Desorption | 0.0 | 0.0 | 0.8 | 0.0 | 0.0 | 0.3 |
|  | 0.0 | 0.0 | 0.6 | 0.0 | 0.0 | 0.3 |
|  | 0.0 | 0.0 | 0.6 | 0.0 | 0.0 | 0.3 |
| % Desorption Average | 0.0 | 0.0 | 0.7 | 0.0 | 0.0 | 0.3 |
| % Efficiency | 99.5 | 100.0 | 99.3 | 99.5 | 98.4 | 98.9 |

Inclusion Rate: 1 kg/ton
Rodenticide Concentration: 5000 ppb
Adsorption pH: 4
Desorption pH: 6.5

Example 3: Rodenticide Absorbent Sample
Description—MYCO-AD D-F 5 May 2016
16E05JFX The sample is formed from Bentonite. The results of these tests are performed under ambient temperature and humidity. These results relate only to the samples tested.

|  | Brodifacoum | Bromadiolon | Coumatetralyl | Difenacoum | Flocoumafen | Warfarin |
|---|---|---|---|---|---|---|
| % Adsorption | 99.8 | 100.0 | 0.8 | 99.8 | 93.7 | 6.5 |
|  | 99.5 | 100.0 | 1.0 | 99.7 | 91.1 | 5.3 |
|  | 99.7 | 100.0 | 0.6 | 99.8 | 90.7 | 4.6 |
| % Adsorption Average | 99.7 | 100.0 | 0.8 | 99.8 | 91.8 | 5.5 |
| % Desorption | 1.1 | 99.8 | 0.7 | 12.4 | 1.9 | 6.5 |
|  | 1.3 | 99.8 | 1.0 | 12.4 | 1.9 | 5.4 |
|  | 1.3 | 99.9 | 0.6 | 14.7 | 3.4 | 4.4 |
| % Desorption Average | 1.2 | 99.8 | 0.8 | 13.2 | 2.4 | 5.4 |
| % Efficiency | 98.5 | 0.2 | 0.0 | 86.6 | 89.4 | 0.1 |

Inclusion Rate: 1 kg/ton
Rodenticide Concentration: 5000 ppb
Adsorption pH: 4
Desorption pH: 6.5

Example 4: Rodenticide Absorbent Sample Description—MYCO-AD D-F 5 May 2016 16E05JFX The sample is formed from Bentonite. The results of these tests are performed under ambient temperature and humidity. These results relate only to the samples tested.

|  | Brodifacoum | Bromadiolon | Coumatetralyl | Difenacoum | Flocoumafen | Warfarin |
|---|---|---|---|---|---|---|
| % Adsorption | 100.0 | 100.0 | 1.3 | 99.9 | 97.7 | 6.7 |
|  | 100.0 | 100.0 | 0.2 | 99.9 | 98.6 | 7.5 |
|  | 100.0 | 100.0 | 0.0 | 99.9 | 98.4 | 7.8 |
| % Adsorption Average | 100.0 | 100.0 | 0.5 | 99.9 | 98.2 | 7.3 |
| % Desorption | 1.0 | 99.9 | 0.5 | 15.1 | 2.1 | 6.6 |
|  | 0.8 | 100.0 | 0.5 | 11.9 | 2.3 | 7.5 |
|  | 1.0 | 99.1 | 0.5 | 14.5 | 1.7 | 7.8 |
| % Desorption Average | 0.9 | 99.7 | 0.5 | 13.8 | 2.0 | 7.3 |
| % Efficiency | 99.1 | 0.3 | 0.0 | 86.1 | 96.2 | 0.0 |

Inclusion Rate: 2.5 kg/ton
Rodenticide Concentration: 5000 ppb
Adsorption pH: 4
Desorption pH: 6.5

Example 5

In one embodiment, a rodenticide binding system may include an amount of an organoclay and an amount of a synthetic hectorite clay, each as described hereinabove.

In some embodiments, the rodenticide binding system may be as follows:

| Component | Amount (weight percent) |
|---|---|
| Organoclay | 80.0 to 99.9 |
| Synthetic Hectorite Clay | 0.1 to 20.0 |

Example 6

In another embodiment, a rodenticide binding system may include an amount of a hydrated sodium calcium aluminosilicate clay and an amount of a synthetic hectorite clay, each as described herein above.

In some embodiments, the rodenticide binding system may be as follows:

| Component | Amount (weight percent) |
|---|---|
| Hydrated Sodium Calcium Aluminosilicate Clay | 80.0 to 99.9 |
| Synthetic Hectorite Clay | 0.1 to 20.0 |

Example 7

In yet one other embodiment, a rodenticide binding system may include an amount of an organoclay, and amount of a hydrated sodium calcium aluminosilicate clay, and an amount of a synthetic hectorite clay, each as described hereinabove.

In some embodiments, the rodenticide binding system may be as follows:

| Component | Amount (weight percent) |
|---|---|
| Organoclay | 0.9 to 99.0 |
| Hydrated Sodium Calcium Aluminosilicate Clay | 0.9 to 99.0 |
| Synthetic Hectorite Clay | 0.1 to 20.0 |

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of ameliorating a malady associated with a rodenticide, comprising:
    combining a composition with an animal feed, wherein the composition comprises:
        an organoclay;
        bentonite;
        hectorite; and
        humic acid;
    providing the animal feed to an animal for consumption by the animal, wherein the composition binds at least one rodenticide associated with the animal after consumption of the animal feed by the animal, wherein the at least one rodenticide comprises Brodifacoum, Bromadiolon, Coumatetralyl, Difenacoum, Flocoumafen, or Warfarin.

2. The method of claim 1, wherein the animal comprises a monogastric animals and/or ruminant animals.

3. The method of claim 1, wherein the composition binds at least one rodenticide associated with the animal after consumption of the animal feed by the animal with a greater than 90% efficiency.

4. The method of claim 1, wherein the bentonite comprises between about 50% and about 75% of the composition.

5. The method of claim 1, wherein the organoclay comprises between about 20% and about 40% of the composition.

6. The method of claim 1, wherein the hectorite comprises between about 0.5% and about 5.0% of the composition.

7. The method of claim 1, wherein the hectorite comprises between about 0.5% and about 5.0% of the composition.

8. The method of claim 1, wherein the humic acid is provided by Leonardite.

* * * * *